Figure 1:
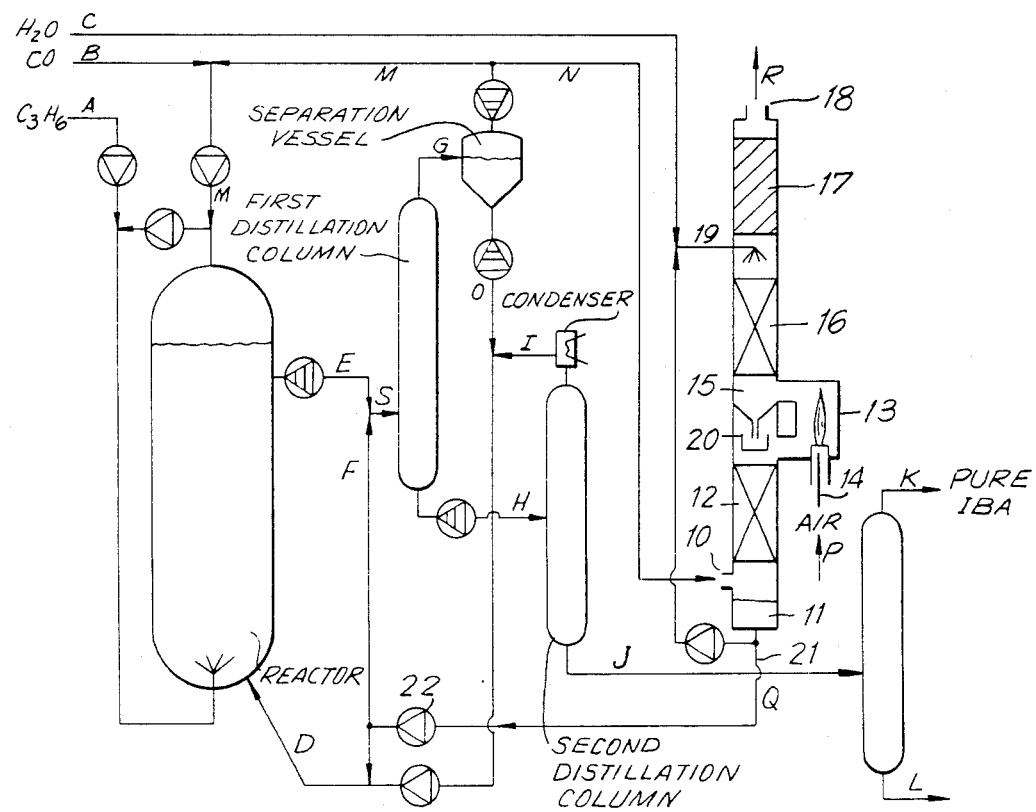

United States Patent [19]

Besecke et al.

[11] Patent Number: 4,504,675
[45] Date of Patent: Mar. 12, 1985

[54] METHOD FOR MAKING ISOBUTYRIC ACID OR ESTERS THEREOF

[75] Inventors: Siegmund Besecke, Seeheim-Jugenheim; Hermann-Josef Siegert, Darmstadt; Günter Schröder, Ober-Ramstadt, all of Fed. Rep. of Germany

[73] Assignee: Röhm GmbH, Darmstadt, Fed. Rep. of Germany

[21] Appl. No.: 436,467

[22] Filed: Oct. 25, 1982

[30] Foreign Application Priority Data

Nov. 14, 1981 [DE] Fed. Rep. of Germany ....... 3145311

[51] Int. Cl.$^3$ .................. C07C 51/14; C07C 67/38
[52] U.S. Cl. .................................. 560/233; 562/521
[58] Field of Search ........................ 560/233; 562/521

[56] References Cited

U.S. PATENT DOCUMENTS

| | | | |
|---|---|---|---|
| 3,052,698 | 9/1962 | Friedman et al. | 560/233 |
| 3,461,157 | 8/1969 | Olivier et al. | 560/233 |
| 4,255,591 | 3/1981 | Makin et al. | 560/233 |
| 4,303,594 | 12/1981 | Norton et al. | 260/546 |

OTHER PUBLICATIONS

*Journal of Organic Chemistry*, vol. 37, No. 12, (1972), pp. 1971–1975, Norell, J. R.

*Primary Examiner*—Natalie Trousof
*Assistant Examiner*—Patricia M. Scott
*Attorney, Agent, or Firm*—Curtis, Morris & Safford

[57] ABSTRACT

What is disclosed is a process for the continuous production of isobutyric acid or an alkyl ester thereof by the Koch synthesis, which process comprises reacting propylene, carbon monoxide, and water or an alkanol in the presence of hydrogen fluoride in at least one reaction space containing a liquid phase and a gas phase under high pressure, releasing said pressure at least partially, whereby a gas containing organic compounds from said synthesis evolves from said liquid phase, adding oxygen to said evolved gas and at least partially combusting the organic compounds contained therein, then contacting the evolved gas containing the at least partially combusted organic compounds with at least a portion of the water or alkanol to be reacted with said propylene and carbon monoxide, whereby at least a portion of said combusted organic compounds are absorbed by said water or alkanol, returning said water or alkanol containing the absorbed combusted organic compounds to said reaction space, and discharging any unabsorbed gas from the reaction system.

10 Claims, 2 Drawing Figures

METHOD FOR MAKING ISOBUTYRIC ACID OR ESTERS THEREOF

The present invention relates to an improved method for the continuous preparation of isobutyric acid or an ester thereof by the Koch synthesis from propylene, carbon monoxide, and water or an alcohol, preferably a lower alkanol, in the presence of hydrogen fluoride as a catalyst. More in particular the invention relates to an improved method which can be practised on an industrial scale.

While the basic process for the preparation of isobutyric acid and its esters by the Koch synthesis is known from various publications, the problems which are encountered in working up secondary constituents of the reaction mixture have not been dealt with so far. The present invention particularly concerns the problem of purging the gaseous component of the reaction mixture of secondary constituents present therein.

The gaseous starting materials of the Koch synthesis, propylene and carbon monoxide, always contain small amounts of impurities such as carbon dioxide, hydrogen, methane and other saturated hydrocarbons, nitrogen, etc. Moreover, gaseous byproducts such as isopropyl fluoride may be formed during the reaction, and these will not react further, or then only partially. Since the isobutyric acid or isobutyric ester reaction product is formed in the liquid phase of the reaction mixture and is recovered from that phase, the gaseous phase of the reaction mixture in principle need not be replaced if the portions consumed during the reaction are continuously replenished. If they are, the concentration of said secondary constituents gradually increases.

In a continuous process the practice is to eliminate such constituents after they have reached a certain concentration by the continuous withdrawal of a portion of the gaseous phase in which the amount of the secondary constituents corresponds to that present in the continuous feed and that newly formed. However, the portion of the gas phase withdrawn contains substantial amounts of hydrogen fluoride which must not be allowed to get into the atmosphere. It must therefore be extracted from the off gas, for example with milk of lime. However, this is an unsatisfactory solution because of the loss of hydrogen fluoride.

A very detailed review by Y. Takezaki of the Koch synthesis of isobutyric acid using hydrogen fluoride as the Koch catalyst appeared in the Bulletin of The Japan Petroleum Institute, 8, 31–38 (1966). However, the problem of the removal of secondary constituents is not dealt with in that article. This is true also of the descriptions of this process given in U.S. Pat. Nos. 2,975,199 and 3,052,698 and in European Pat. No. 31,886. While the last mentioned patent does mention the recycling to the reactor of the low-boiling constituents of the reaction mixture, and in particular hydrogen fluoride and propylene, as well as the fractionation of byproducts such as isobutyric fluoride, no provision is made for the elimination of constituents of the gas phase. The hydrogen fluoride adhering to the reaction product is to be retained by absorption on bauxite. Actually, only traces of hydrogen fluoride can be removed in this way.

U.S. Pat. No. 4,303,594 describes a process for the production of isobutyric anhydride by the Koch synthesis from propylene, carbon monoxide, and water in the presence of hydrogen fluoride as the Koch catalyst. An off-gas stream is taken from the reactor and the gaseous hydrogen fluoride which it carries is removed therefrom by scrubbing with water. The aqueous solution of hydrogen fluoride is used in the synthesis of isobutyric anhydride. Organic fluorine compounds having hydrolytic stability, such as isopropyl fluoride, may be formed as byproducts of the Koch synthesis and these will not be absorbed by the water flowing through the absorber. The organic fluorine compounds thus get into the atmosphere with the unabsorbed off gas, which is something that should be prevented for reasons of environmental protection.

The object of the present invention is to improve the Koch synthesis of isobutyric acid or its alkyl esters by the elimination of secondary constituents of the gaseous component of the reaction mixture so that no hydrogen fluoride and no organic fluorine compounds such as isopropyl fluoride or isobutyric acid fluoride get into the atmosphere, or are lost as unusable reaction products, or must be worked up at an expenditure of energy or materials.

This object is accomplished by adding oxygen to the gas withdrawn from the reaction space or from a processing arrangement and at least partially burning the organic compounds carried by said gas, whereby the organic fluorine compounds form hydrogen fluoride, and then contacting the gases of combustion in an absorber with water or an alkanol and conducting the liquid containing the hydrogen fluoride to the reaction space. Since the reaction requires water or a lower alkanol anyway, the use of water or an alkanol in the recovery of hydrogen fluoride from the withdrawn portion of the gas does not involve an additional expenditure of materials. The hydrogen fluoride is scrubbed from the off gas stream to such an extent that the residual amounts remaining in the off gas are negligible and, if necessary, can be retained on a basic absorbent such as bauxite, lime, or milk of lime in an absorption column disposed downstream. The water or alkanol with the absorbed hydrogen fluoride can be fed directly into the reaction mixture without requiring prior fractionation, concentration, or other conditioning. Loading of the off gas or waste water from the manufacturing plant with hydrogen fluoride thus is positively prevented.

There are various embodiments of the Koch synthesis. The conventional Koch synthesis is carried out in two steps. In the first step, an olefin is reacted with carbon monoxide in the presence of a Koch catalyst. The intermediate product formed is reacted further in a second step with water or an alkanol to give carboxylic acid or esters thereof. The two process steps are carried out in separate reaction spaces. In the single step variant, water or an alkanol is added to the reaction mixture at the outset so that carboxylic acid or esters thereof are formed immediately. The invention can be used with both variants of the process by feeding the water or alkanol carrying hydrogen fluoride to the appropriate reaction space.

The invention is used to great advantage in the preparation of free isobutyric acid, the water used in the reaction serving as absorbent.

Figure 2:
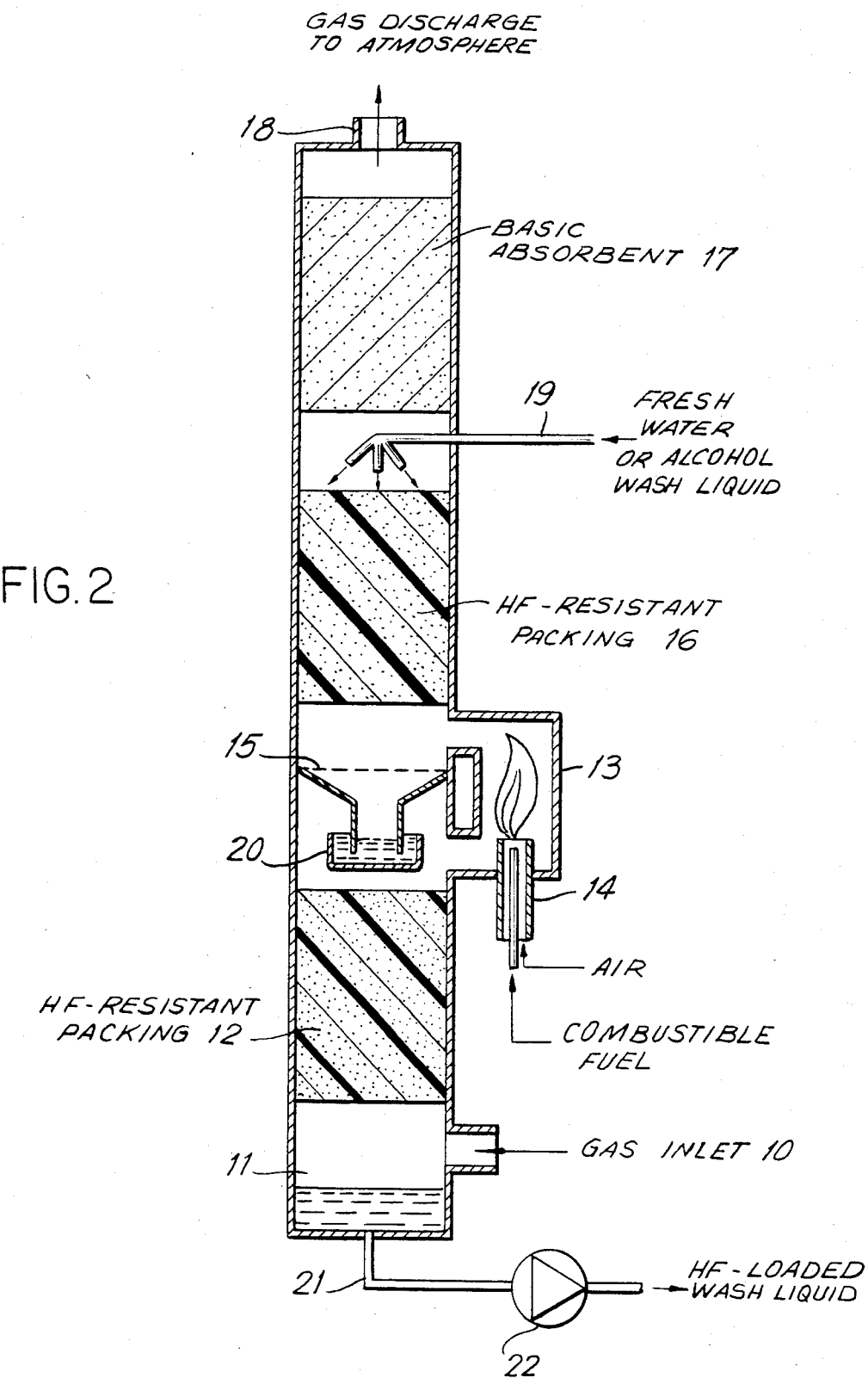

A better understanding of the invention and of its many advantages will be had by referring to the accompanying drawings in which:

FIG. 1 is a flow diagram illustrating the production of isbutyric acid by the carboxylation of propylene in the presence of HF according to the Koch synthesis wherein hydrogen fluoride and organic fluorine compounds in off-gas from the reactor are treated according to the process of the present invention; and FIG. 2 is a flow diagram illustrating such treatment of the off-gas in more detail and schematically illustrating suitable apparatus therefor.

For the preparation of isobutyric acid or its esters according to the invention, at least 1 mole of water or 1 mole of an alkanol and from 5 to 20 moles of hydrogen fluoride are used per mole of propylene used. The preferred alkanol is methanol. Other suitable alkanols are ethanol, propanol, isopropanol, and n-butanol or isobutanol. The total amount of water or alkanol used in the reaction is preferably used as scrubbing liquid in the absorber; however, this amount need not be greater than 2 moles per mole of propylene used.

The Koch synthesis of isobutyric acid or its esters is carried out under pressure. The usual pressures for this reaction range from 50 to 150 bars. A portion of the gas phase may be withdrawn from the pressurized reactor, conducted to an absorber while maintaining the pressure, and contacted with water or alkanol pumped into the absorber. This offers the advantage that the corrosive mixture of water or alkanol and hydrogen fluoride need not be piped to the reaction chamber by means of a pressure pump. However, the absorber must then be of pressure-resistant construction. An expansion valve disposed at the absorber outlet also permits the flow rate of the off gas to be adjusted. The expanded off gas may be conducted through an absorber filled with the previously mentioned basic packing for removal of residual hydrogen fluoride. The exit gas may be mixed with air and ignited for combustion of the organic fluorine compounds. If it will not burn of its own, a combustible gas may be admixed with it. The hydrogen fluoride formed may be removed in a second absorber by scrubbing with water.

In the flashing of the liquid phase of the reaction mixture for the purpose of further working up, and possibly in the fractional distillation of the liquid reaction mixture, the release from pressure causes previously dissolved gaseous constituents, and particularly hydrogen fluoride, to be liberated. When a substantial amount of the gaseous contaminants to be purged is so released, it is sufficient to conduct only the gases so evolved in flashing through the absorber. There will then be no need to withdraw gas directly from the pressurized zone. The pressure may be reduced in several stages, for example, first to from 2 to 10 bars, then to atmospheric pressure, with gases evolving each time. In general, it is not economical to compress this corrosive gas in order to be able to return it to the reaction chamber. For this reason it is usually piped to the absorber and, after combustion of the organic constituents and removal of the hydrogen fluoride by scrubbing, discharged to the atmosphere.

When the stream of gas evolved upon the flashing of the liquid phase is not sufficient for the purging of the gaseous contaminants formed, a portion of the gas phase must be withdrawn from the pressurized zone. When the gas phase is not scrubbed under pressure, it is expanded and preferably combined with the gas evolving from the liquid phase. In the scrubbing of the expanded gas, water or alkanol carrying hydrogen fluoride is obtained which is piped to the pressurized zone by means of a suitable pump for liquids.

In general it is preferred to remove the free hydrogen fluoride from the gas stream by scrubbing in the first absorber and, after combustion of the organic fluorine compounds, to remove the hydrogen fluoride thus formed by scrubbing in a second absorber. However, it is also possible to conduct the entire gas stream first to the combustion chamber and then to remove the hydrogen fluoride by scrubbing in a single absorber.

In the combustion chamber, oxygen, preferably in the form of air, is mixed with the gas, and the organic constituents are burned. The amount of oxygen should be sufficient to permit complete combustion of all combustible constituents to form water or carbon dioxide. From 100 to 200 percent of the calculated theoretical amount of oxygen will usually suffice for the purpose. In practice, between 100 and 130 percent, and preferably between 102 and 120 percent, of that amount is generally used. In general, combustion occurs in a flame, temperatures of 2000° C. and higher being reached in the process. However, combustion may also be carried out over an oxidation catalyst. Platinum or palladium catalysts, for example, on carriers such as alumina are suited for this purpose. For the initiation of catalytic combustion, the gas should be preheated, preferably to 300° to 700° C. This may be done by indirect heating through a heat exchanger. The gases of combustion leaving the catalyst bed, or other gases burning with a flame, may then be used as heating media. Alternatively, the gas to be burned may be mixed directly with another hot gas and the gas mixture formed may then be conducted over the catalyst.

As a rule, the gas withdrawn will be formed to a large extent of carbon monoxide, which burns readily in a flame after it has been mixed with oxygen. However, if the gas contains a substantial proportion of noncombustible constituents because of the use of impure starting gases, for example, the caloric value of the gas may be too low to sustain a flame or catalytic oxidation. In that case, it will be advisable to add another combustible substance, preferably natural gas, hydrogen, or heating oil, to the gas in such an amount that the caloric value is sufficient to sustain a flame. The caloric value of the gas should be at least 2000 kcal/kg, and preferably between 4000 and 6000 kcal/kg. In determining the amount of oxygen to be added, the additional combustible substance added must, of course, be taken into consideration. If caloric values of this order of magnitude are attained, complete combustion of the fluorine containing organic compounds to carbon dioxide and gaseous hydrogen fluoride is assured.

It is advisable to divide the absorber into two stages and to place the combustion stage between them. A suitable apparatus is shown in cross section in FIG. 2 of the drawing. The gas stream enters antechamber 11 of first absorber stage 12. After passing through absorber 12, the gas reaches combustion chamber 13, into which oxygen or air and, if indicated, a combustible substance are introduced through line 14. The gas mixture is burned and after combustion enters antechamber 15 of second absorber stage 16, from which it passes into a third absorber stage 17, where residual amounts of hydrogen fluoride are retained on a solid or liquid, suitably basic, absorbent. Through line 18, the gas is then discharged to the atmosphere. The water or alkanol used as scrubbing liquid is piped through line 19 to second absorber stage 16 and then passes from antechamber 15 through overflow 20 into the lower absorber stage 12. It collects in antechamber 11 and from there is piped through line 21 and, if necessary, pressure pump 22 to the reaction chamber.

When the two absorber stages 12 and 16 are operated at the same pressure, overflow 20 disposed between them will prevent direct passage of the gas stream and force the latter to pass through combustion chamber 13. Optionally, first absorber stage 12 may be operated under pressure. In that case, an expansion valve (not shown) is disposed in the passage to combustion chamber 13 and the scrubbing liquid is piped from antechamber 15 to the top of the absorber 12 by means of a pressure pump (cf. FIG. 1).

As a rule, absorbers 12 and 16 contain conventional packing. Like all other parts of the absorption unit, this packing is fabricated from a material that is resistant to hydrogen fluoride or hydrofluoric acid, respectively. Suitable materials include aluminum, nickel-chromium-iron alloys, and polytetrafluroethylene or similar fluorinated polymers.

The amount of gas withdrawn should be large enough for the fraction of gaseous contaminants and undesired gaseous byproducts which it carriers to correspond to that present in the continuous feed and newly formed. Since some of the propylene and carbon monoxide is always lost with the gaseous contaminants, the partial pressure of the latter is advantageously held high. For this reason, the partial pressure of the gaseous contaminants in the gas phase in the reactor should be allowed to rise to a level that falls just short of having an adverse effect on the progress of the reaction. Under steady state operating conditions, the partial pressure of the gaseous contaminants will be constant. That partial pressure should not exceed 30 bars, if possible. The total pressure should be held so high that, after subtraction of the partial pressure of the gaseous contaminants, the pressure of the reacting gases (propylene, carbon monoxide and hydrogen fluoride) is high enough to assure the desired reaction rate.

A better understanding of the present invention will be had by referring to following Example 1, which describes a continuous Koch synthesis performed in otherwise conventional apparatus, but which incorporates a combustion and absorption unit, as shown in the accompanying drawing, wherein the process of the present invention is performed. The reference letters and numerals of the Example refer to FIGS. 1 and 2 of the drawings.

EXAMPLE 1

Propylene and CO were continuously introduced into a reactor through lines A and B respectively and, with a dwell time of the liquid phase in the reactor of five minutes, were reacted at a temperature of 120° C. and a pressure of 120 bar. The gas phase was recirculated by means of a pump.

After decompression of the reaction product to a pressure of 3 bar, the product was removed from the reactor through a line E and, after admixture thereof with wash water, was introduced through a line S into a first distillation column. HF and leakage gases were distilled off at a pressure of 3 bar and, after condensation, were introduced into a separation vessel through a line G. The sump from the first distillation column was introduced into a second distillation column by way of an expansion valve and a line H. Residual HF and water were distilled off in the second distillation column at atmospheric pressure and condensed in a condenser. From the sump of the second distillation column, isobutyric acid of about 96 percent purity was introduced through a line J into a further distillation column for purification. Pure isobutyric acid was withdrawn from the head of the column through a line K. Small amounts of high-boiling residues were withdrawn from the sump of the column through a line L.

Liquid hydrofluoric acid was removed from the aforementioned separation vessel through a line O, combined with the condensate of the aforementioned second distillation column, which condensate was withdrawn from the aforementioned condenser through a line I, and this mixture was reintroduced into the reactor through a line D. A major portion of the gases drawn off in the separation vessel were reintroduced directly into the reactor through a line M after compression. The remaining minor portion of these gases were introduced into adsorber apparatus 12, 16, 17 of the accompanying drawings through a line N (=gas inlet 10 of the accompanying drawings) at a temperature of 20° C. and at atmospheric pressure. Absorber stages 12 and 16 contain packing bodies over which water trickles through a line C (=inlet line 19 of the accompanying drawings). Overflow 20 of the accompanying drawing is interposed between absorber stages 12 and 16 and is impermeable to gases which, instead, flow through a combustion chamber by-pass (=combustion chamber 13 of the accompanying drawings). Air is introduced into combustion chamber 13 through a line P (=line 14 of the accompanying drawings). The combustible component of the gases introduced into combustion chamber 13 is combusted therein and is passed through absorber stage 17 of the accompanying drawing. From stage 17, the gases escape through a bauxite packing through a discharge line R (=discharge line 18 of the accompanying drawings).

The wash water containing HF is accumulated at the foot of absorber 12, 16, 17, in part recirculated to the absorber (cf. FIG. 1), and in part removed through a line Q (=discharge line 21 of the accompanying drawings) containing high pressure pump 22. On the discharge side of pump 22, the line divides (cf. FIG. 1) and part of the wash water is returned through aforementioned line D to the reactor and the other part through aforementioned lines F and S into the first distillation column.

The contents of the various lines present in the arrangement discussed above are set out below in Table I, wherein:

TABLE I

| Line | Moles per Minute of Component in Line | | | | | | | | | | | | | |
| --- | --- | --- | --- | --- | --- | --- | --- | --- | --- | --- | --- | --- | --- | --- |
| | HF | CO | $C_3H_6$ | $H_2O$ | IBA | IPF | IBF | IBE | Olig | $H_2$ | $C_3H_8$ | $N_2$ | $O_2$ | $CO_2$ |
| A | | | 1.01 | | | | | | | | 0.06 | | | |
| B | | 1.07 | | | | | | | | 0.002 | | 0.005 | 0.001 | 0.012 |
| C(=19) | | | | 0.746 | | | | | | | | | | |
| D | 9.64 | | 0.003 | 0.99 | | | | | | | | | | |
| E | 9.93 | 0.72 | 0.004 | 0.064 | 0.86 | 0.015 | 0.06 | 0.033 | 0.027 | 0.020 | 0.62 | 0.052 | 0.010 | 0.120 |
| F | 0.005 | | | 0.15 | | | | | | | | | | |
| G | 9.82 | 0.72 | 0.037 | | | 0.015 | | | | 0.020 | 0.62 | 0.052 | 0.010 | 0.120 |
| H | 0.17 | | | 0.154 | 0.94 | | | | 0.027 | | | | | |

TABLE I-continued

| Line | HF | CO | C₃H₆ | H₂O | IBA | IPF | IBF | IBE | Olig | H₂ | C₃H₈ | N₂ | O₂ | CO₂ |
|---|---|---|---|---|---|---|---|---|---|---|---|---|---|---|
| I | 0.17 | | | 0.154 | | | | | | | | | | |
| J | | | | | 0.94 | | | | 0.027 | | | | | |
| K | | | | | 0.93 | | | | | | | | | |
| L | | | | 0.01 | | | | | 0.027 | | | | | |
| M | 0.35 | 0.63 | 0.030 | | | 0.012 | | | | 0.018 | 0.54 | 0.045 | 0.009 | 0.108 |
| N(=10) | 0.035 | 0.070 | 0.004 | | | 0.0012 | | | | 0.002 | 0.06 | 0.005 | 0.001 | 0.012 |
| O( ) | 9.43 | 0.02 | 0.003 | | | 0.0015 | | | | | 0.018 | 0.002 | | |
| P(=14) | | | | 0.041 | | | | | | | | 1.62 | 0.43 | |
| Q(=21) | 0.036 | | | 0.99 | | | | | | | | | | |
| R(=18) | | | | 0.059 | | | | | | | | 1.63 | 0.072 | 0.278 |

IBA = isobutyric acid
IPF = isopropyl fluoride
IBF = isobutyric acid fluoride
IBE = isobutyric acid isopropyl ester
Olig = high-boiling oligomeric byproducts

What is claimed is:

1. In a process for the continuous production of isobutyric acid or an alkyl ester thereof by the Koch synthesis, by reacting propylene, carbon monoxide, and water or an alkanol in the presence of hydrogen fluoride in at least one reaction space containing a liquid phase and a gas phase under high pressure, the improvement which comprises releasing said pressure at least partially whereby a gas containing organic compounds from said synthesis evolves from said liquid phase, adding oxygen to said evolved gas and at least partially combusting the organic compounds contained therein, then contacting the evolved gas containing the at least partially combusted organic compounds with at least a portion of the water or alkanol to be reacted with said propylene and carbon monoxide, whereby at least a portion of said combusted organic compounds are absorbed by said water or alkanol, returning said water or alkanol containing the absorbed combusted organic compounds to said reaction space, and discharging any unabsorbed gas from the reaction system.

2. A process as in claim 1 wherein a portion of the gas phase present in said reaction space is withdrawn therefrom and admixed with said evolved gas, oxygen is added to this mixture, and said mixture is then combusted.

3. A process as in claim 1 wherein a combustible substance is added to said evolved gas prior to combustion to increase the caloric value thereof.

4. A process as in claim 2 wherein a combustible substance is added to said mixture prior to combustion to increase the caloric value thereof.

5. A process as in claim 1 wherein oxygen is added to said evolved gas in an amount which is 100 to 200 percent of the theoretical amount required for the complete combustion of combustible organic compounds contained therein.

6. A process as in claim 2 wherein oxygen is added to said evolved gas in an amount which is 100 to 200 percent of the theoretical amount required for the complete combustion of combustible organic compounds contained therein.

7. A process as in claim 1 wherein said unabsorbed gas is contacted with a basic absorbent prior to discharge from the reaction system.

8. A process as in claim 2 wherein said unabsorbed gas is contacted with a basic absorbent prior to discharge from the reaction system.

9. A process as in claim 1 wherein said evolved gas is additionally contacted with at least a portion of the water or alkanol to be reacted with said propylene and carbon monoxide prior to combusting the organic compounds contained in said evolved gas.

10. A process as in claim 2 wherein said mixture of withdrawn gas and evolved gas is additionally contacted with at least a portion of the water or alkanol to be reacted with said propylene and carbon monoxide prior to combusting the organic compounds contained in said mixture.

* * * * *